United States Patent
Cui et al.

(10) Patent No.: US 9,512,458 B2
(45) Date of Patent: Dec. 6, 2016

(54) ELECTROCHEMICAL BIOSENSOR WITH SAMPLE INTRODUCTION CHANNEL CAPABLE OF UNIFORM INTRODUCTION OF SMALL AMOUNT OF SAMPLE

(75) Inventors: Gang Cui, Seoul (KR); Jae Hyun Yoo, Gangwon-do (KR); Ju Yong Kim, Gyeonggi-do (KR); Keun Ki Kim, Seoul (KR); Moon Hwan Kim, Seoul (KR); Hakhyun Nam, Seoul (KR); Geun Sig Cha, Seoul (KR)

(73) Assignee: I-SENS, INC., Seoul (KR)

( * ) Notice: Subject to any disclaimer, the term of this patent is extended or adjusted under 35 U.S.C. 154(b) by 630 days.

(21) Appl. No.: 12/740,016

(22) PCT Filed: Oct. 24, 2008

(86) PCT No.: PCT/KR2008/006313
§ 371 (c)(1),
(2), (4) Date: Apr. 27, 2010

(87) PCT Pub. No.: WO2009/057917
PCT Pub. Date: May 7, 2009

(65) Prior Publication Data
US 2011/0011739 A1    Jan. 20, 2011

(30) Foreign Application Priority Data
Oct. 29, 2007 (KR) .................. 10-2007-0108758

(51) Int. Cl.
*C12Q 1/00* (2006.01)
*G01N 27/327* (2006.01)
*B01L 3/00* (2006.01)

(52) U.S. Cl.
CPC ............. *C12Q 1/006* (2013.01); *B01L 3/5027* (2013.01); *G01N 27/3272* (2013.01);
(Continued)

(58) Field of Classification Search
CPC . G01N 27/3272; C12Q 1/006; B01L 3/5027; B01L 2300/0825; B01L 2300/0887; B01L 2300/0645; B01L 2400/0406
USPC .......................... 204/403.01, 403.02, 403.04
See application file for complete search history.

(56) References Cited

U.S. PATENT DOCUMENTS 6,156,270 A    12/2000   Buechler
7,258,769 B2*  8/2007    Cui et al. ................. 204/403.14
(Continued)

FOREIGN PATENT DOCUMENTS

CN    1815236 A    8/2006
EP    1113263 A2   4/2001
(Continued)

OTHER PUBLICATIONS

"PCT International Search Report dated Apr. 8, 2008 for PCT/KR2008/006313, from which the instant application is based," 2 pgs.
(Continued)

*Primary Examiner* — Louis Rufo
(74) *Attorney, Agent, or Firm* — Fredrikson & Byron, P.A.

(57) ABSTRACT

Disclosed is an electrochemical biosensor having a sample introduction channel in which an insulator is employed to introduce a small amount of a sample uniformly and accurately and to adjust an area of a working electrode, thereby guaranteeing the accurate quantitative analysis of a sample. Provided with a sample collection barrier at a sample entrance, the biosensor allows a sample to be introduced at higher accuracy and to be analyzed with higher reproducibility and reliability.

9 Claims, 4 Drawing Sheets

(52) U.S. Cl.
CPC .............. *B01L 2300/0645* (2013.01); *B01L 2300/0825* (2013.01); *B01L 2300/0887* (2013.01); *B01L 2400/0406* (2013.01)

(56) References Cited

U.S. PATENT DOCUMENTS

| | | | |
|---|---|---|---|
| 2003/0211625 A1 | 11/2003 | Cohan et al. | |
| 2004/0134779 A1* | 7/2004 | Hsu et al. | 204/403.03 |
| 2005/0013731 A1* | 1/2005 | Burke et al. | 422/56 |
| 2005/0029097 A1 | 2/2005 | Cheng et al. | |
| 2006/0131171 A1* | 6/2006 | Kobayashi | 204/403.01 |
| 2006/0175205 A1 | 8/2006 | Cui et al. | |
| 2007/0034512 A1* | 2/2007 | Yamaoka et al. | 204/403.01 |
| 2007/0080076 A1* | 4/2007 | Livache et al. | 205/792 |
| 2008/0006530 A1* | 1/2008 | Winarta et al. | 204/403.01 |
| 2009/0093695 A1* | 4/2009 | Nakamura et al. | 600/347 |

FOREIGN PATENT DOCUMENTS

| | | |
|---|---|---|
| EP | 1182456 A2 | 2/2002 |
| EP | 1486778 A2 | 12/2004 |
| EP | 1635170 A1 | 3/2006 |
| JP | 208716 A | 8/2001 |
| JP | 524822 A | 8/2007 |
| KR | 1020030054204 A | 7/2003 |
| WO | 2004113901 A1 | 12/2004 |
| WO | WO 2007001003 A1 * | 1/2007 |
| WO | 2007148285 A2 | 12/2007 |

OTHER PUBLICATIONS

English Abstract of CN1815236A, Aug. 9, 2006, 1 page.
English Abstract of JP2007524822A, Aug. 30, 2007, 1 page.
English Abstract of JP2001208716A, Aug. 3, 2001, 1 page.

* cited by examiner

Fig. 1
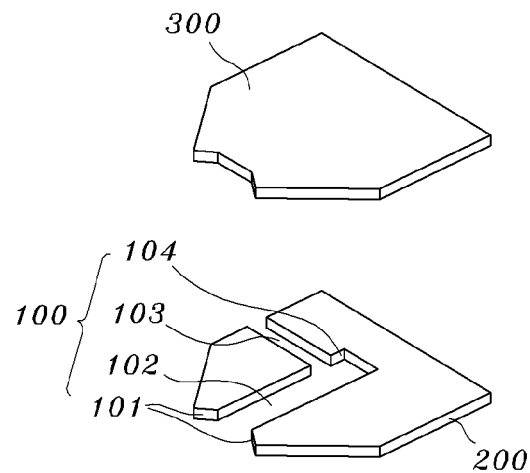
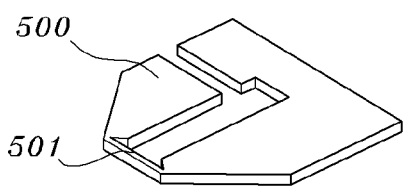
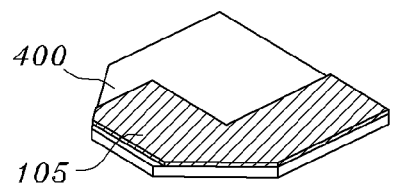
Fig. 2
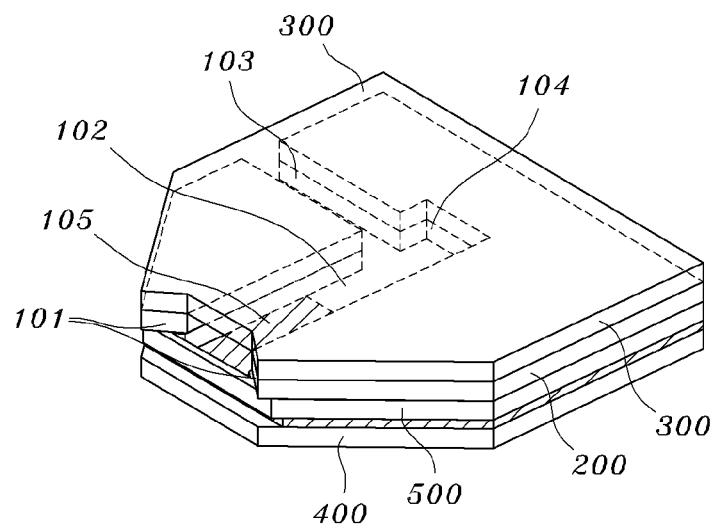

ELECTROCHEMICAL BIOSENSOR WITH SAMPLE INTRODUCTION CHANNEL CAPABLE OF UNIFORM INTRODUCTION OF SMALL AMOUNT OF SAMPLE

RELATED APPLCIATIONS

This application is a 35 U.S.C. 371 national stage filing from International Application No. PCT/KR2008/006313 filed Oct. 28, 2008, which claims priority to Korean Application No. 10-0108758 filed Oct. 29, 2007, the teachings of which are incorporated herein by reference.

TECHNICAL FIELD

The present invention relates to an electrochemical biosensor provided with a sample introduction channel in which an insulator is employed to introduce a small amount of a sample uniformly and accurately and to adjust an area of a working electrode, thereby guaranteeing the accurate quantitative analysis of a sample.

BACKGROUND ART

For the diagnosis and prophylaxis of diabetes mellitus, the importance of periodic monitoring of blood glucose levels has been increasingly emphasized. Nowadays, strip-type biosensors designed for hand-held reading devices, which are usually based on colorimetry or electrochemistry, allow individuals to readily monitor glucose levels in the blood.

The electrochemistry applied to many commercially available biosensors for the analysis of blood glucose levels is explained by the following Reaction Formula I, featuring the use of an electron transfer mediator (M).

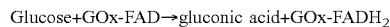

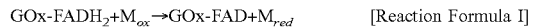  [Reaction Formula I]

wherein, GOx represents glucose oxidase; GOx-FAD and GOx-FADH$_2$ respectively represent an oxidized and a reduced state of glucose-associated FAD (flavin adenine dinucleotide), a cofactor required for the catalyst of glucose oxidase; and M$_{ox}$ and M$_{red}$ denote an oxidized and a reduced state of an electron transfer mediator, respectively.

Examples of the electron transfer mediator for use in electrochemical biosensors include: ferrocene and derivatives thereof; quinines and derivatives thereof; transition metal, containing organic or inorganic compounds, such as hexamine ruthenium, osmium-containing polymers, potassium ferricyanide, etc.; organic conducting salts; and viologen.

In the biosensor, blood glucose levels are measured on the basis of the following principle.

Glucose in the blood is oxidized to gluconic acid by the catalysis of glucose oxidase with the concomitant reduction of the cofactor FAD to FADH$_2$. Then, the reduced cofactor FADH$_2$ transfers electrons to the mediator, so that FADH$_2$ returns to its oxidized state; that is, FAD and the mediator are reduced. The reduced mediator is diffused to the surface of the electrodes. The series of reaction cycles is driven by the anodic potential applied at the working electrode, and redox current proportional to the level of glucose is measured. Over biosensors based on colorimetry, the electrochemical biosensors (that is, based on electrochemistry) have the advantages of not being influenced by oxygen and allowing the use of samples, even if cloudy, without pretreatment thereof.

Sample introduction channels of conventional biosensors are largely divided into "i" type and "—" type.

An "i" type sample introduction channel is typically structured to have an opening at an end of a straight sampling passage so as to induce a capillary phenomenon. However, such an "i" type sample introduction channel is problematic in that, depending on the viscosity thereof, the sample introduced through the straight sampling passage may overflow or may not be able to reach the opening located at the end of the straight channel, incurring non-uniformity in sample amount.

A "—" type sample introduction channel is typically structured to have a passage extending from a lateral side of the sensor to another lateral side. Because it is located at a lateral side and has a "—" type structure, the sample introduction channel is inconvenient for a user to introduce a sample therethrough. In addition, turbulence or eddies form upon sample introduction, making it impossible to introduce a sample in a constant amount.

In order to overcome these problems, suggested is an assay device in which the flow in a reagent chamber with the port narrowing just after the entry of a sample and in a hydrophobic zone is controlled by a time gate, thereby preventing turbulence or eddies (U.S. Pat. No. 6,156,270). However, this assay device is not suitable for use with samples on the microliter scale because a reaction-inducible reagent is mixed with a sample before a detection region and the hydrophobic zone is wide and has a wave form. That is, this assay device is not applicable to the case where the mixing of reagents and a sample and detection reactions must be implemented within a narrow cell.

In a conventional biosensor, a sample introduction channel is constructed in a double-sided tape or a film over a working electrode, an auxiliary electrode or a reference electrode, and is lined with an enzyme reaction solution. The sample introduction channel, however, is disadvantageous in that the sample introduction channel is greatly affected by a cut-out pattern of the double-sided tape or laminated film so that it is non-uniformly lined with the enzyme reaction solution, or the amount of the sample that is introduced is not constant, incurring errors in measurement.

Leading to the present invention, intensive and thorough research into the introduction of a constant amount of a sample into an electrochemical biosensor for accurate analysis resulted in the finding that an insulator with a structural pattern that is aligned with a capillary tube pattern of a medium plate can control turbulence or eddies effectively, thus introducing a sample uniformly into a biosensor and increasing analysis accuracy.

DISCLOSURE OF INVENTION

Technical Problem

It is an object of the present invention to provide a biosensor provided with a sample introduction channel allowing the uniform and accurate introduction of a sample into the biosensor.

Technical Solution

In order to accomplish the above object, there is provided an electrochemical biosensor, comprising: a lower plate, upon which is constructed a working electrode coated with a reagent layer containing an electron transfer mediator and a redox enzyme, and a reference electrode; a middle plate having a precut pattern of sample introduction channel composed of a sample entrance, a sample passage and an air vent; and an upper plate or a cover that forms the sample cell structure, wherein a hydrophobic sample collection barrier formed by the insulator between the lower and middle plates is provided.

Advantageous Effects

Provided with a sample collection barrier at the sample entrance, the insulator, formed between the lower plate and the middle plate, can control the flow of a blood sample into the biosensor and can be readily prepared by screen printing so as to adjust the area of the working electrode which reacts with the sample. Therefore, the biosensor having the sample introduction channel can quantitatively analyze a blood sample at high reproducibility and reliability and can be produced on a mass scale thanks to the simplicity of fabrication thereof.

BRIEF DESCRIPTION OF THE DRAWINGS

FIG. 1 is an exploded perspective view showing a sample introduction channel of an electrochemical biosensor in accordance with an embodiment of the present invention;

FIG. 2 is a perspective view showing the sample introduction channel of the electrochemical biosensor in accordance with an embodiment of the present invention;

BRIEF DESCRIPTION OF THE MARK OF DRAWINGS

Figure 3:
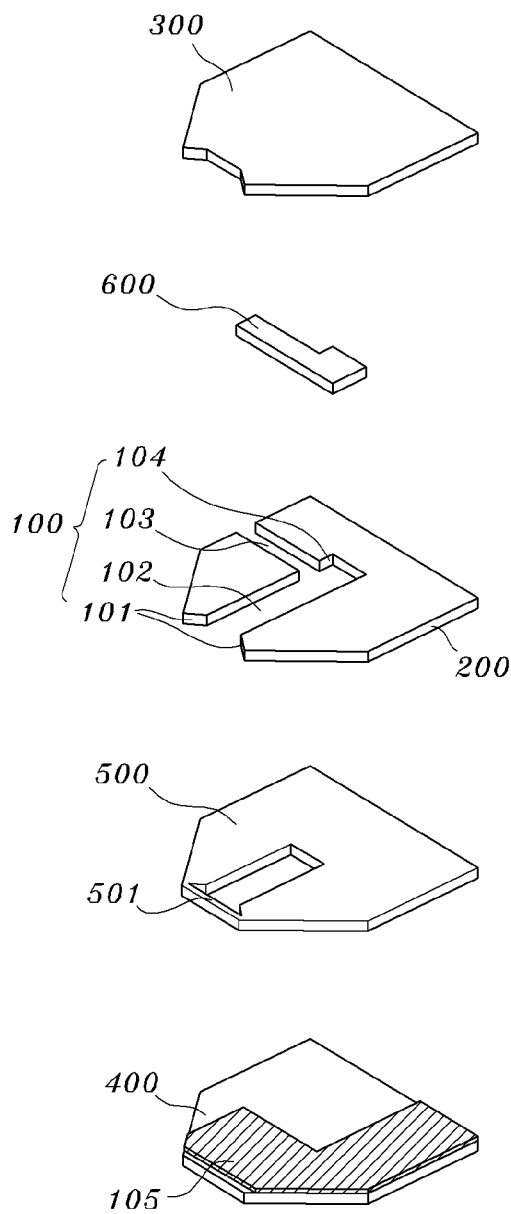
FIG. 3 is an exploded perspective view showing a sample introduction channel of an electrochemical biosensor in accordance with another embodiment of the present invention.

100: sample introduction channel
101: sample entrance
102: sample passage
103: sample vent
104: void space
105: working electrode
106: reference electrode
107: electrode connection
108: fluidity sensing electrode
200: middle plate
300: upper plate
400: lower plate
500: lower insulator
501: sample collection barrier
600: upper insulator

BEST MODE FOR CARRYING OUT THE INVENTION

Reference should now be made to the drawings, in which the same reference numerals are used throughout the different drawings to designate the same or similar components. With reference to FIGS. 1 and 2, a sample introduction channel for an electrochemical biosensor according to an embodiment of the present invention is shown in an exploded perspective view and in an assembled perspective view, respectively.

As shown in FIG. 1, the sample introduction channel of the biosensor according to the present invention comprises a lower plate 400, an insulator 500, a middle plate 200 provided with a sample introduction channel 100, and an upper plate (or cover) 300, which are layered in sequential order.

The sample introduction channel is composed largely of a sample entrance 101, a sample passage 102 and an air vent 103.

As used herein, the term "sample entrance" is intended to refer to an entrance through which a sample is introduced into the biosensor. The term "sample passage" means a passage through which a sample flows into the biosensor so as to react with the working electrode. The term "air vent" is a passage which is configured to allow air to pass therethrough. When a sample passes through the sample entrance and is introduced into the sample passage, the air present in the passage is discharged through the air vent 103, which allows the introduction of a sample through a capillary phenomenon.

In the biosensor according to the present invention, the sample entrance 101 is preferably structured to be tapered toward the sample passage, serving to collect the sample fluid. When a sample flows through the sample entrance into the sample passage, the sample entrance can guide the sample fluid into the sample passage without turbulence or eddies because it narrows toward the sample passage.

Also, a sample collection barrier 501 is provided in the insulator 500 at a position corresponding to an end of the sample entrance of the middle plate 200, as shown in FIG. 1.

When a blood sample is introduced from the sample entrance to the sample passage, the sample collection barrier 501 serves to collect the blood sample in a sufficient amount to generate an effective signal, so that it can be uniformly distributed over the sample passage. As seen in FIG. 1, the sample collection barrier 501 may be formed using the insulator 500. In order to play this role, the sample collection barrier 501 is preferably 1~10 μm high. The sample collection barrier reduces inaccuracy resulting from the non-uniform introduction of the sample, thus allowing accurate analysis.

In the biosensor according to the present invention, the sample passage 102 is preferably crossed with the air vent 103.

By the term "crossed with" as used herein, it is meant that the sample passage 102 and the air vent 103 are not linearly arranged, but intersect each other at a predetermined point.

The ratio between the widths of the sample passage 102 and the air vent 103 is no more than 1:2, and is preferably in the range from 1:5 to 1:2, in order to allow the rapid introduction of a sample into the biosensor. A ratio below 1:2 ensures the containment of an exact amount of a sample in the sample entrance, and allows the sample to proceed to the air vent at a high speed. In FIG. 1, the angle of communication ($\phi$) between the sample passage 102 and the air vent 103 is shown to be 90°. But the angle may be varied within a range from about 45° to 135°, preferably within a range from about 60° to 105°, and most preferably within a range from about 75° to 105°.

The sample passage 102 preferably has a capacity for retaining 0.1~3.0 μl of a sample. More preferably, the capacity is in the range from 0.1 to 1.0 μl, and most preferably in the range from 0.3 to 0.7 μl. A sample volume less than 0.1 μl is too small to give an accurate measurement within the error range of the biosensor. Conversely, a sample volume greater than 3.0 μl is excessive for sampling. In an embodiment of the present invention, even an amount of as small as 0.2 μl is sufficient to ensure accurate measurement.

A void space 104 may be provided at the cross between the sample passage and the air vent. Providing an extra space at the position wherein the sample passage is crossed with or intersects the air vent, the void space 104 serves to prevent the formation of air packets, which may often form at the point of communication between the sample passage and the air vent. At the cross (or intersection), the sample flowing through the sample passage is in contact with the electrodes. The formation of air packets may result in inaccurate measurements. The void space 104, as shown in FIG. 1, may be formed as an extension of the sample passage, but is not limited thereto. For example, the void space may be formed at the same angle as the angle between the sample passage 102 and air vent 103.

In the biosensor according to the present invention, as shown in FIG. 1, the sample passage and the air vent formed in the insulator 500 preferably have the same structure as those formed in the middle plate 200.

The insulator is screen-printed on the lower plate in such a manner that a sample passage is formed in the insulator in alignment with the sample passage of the middle plate. Thus, the exposed area of the working electrode 105 through the sample passage can be more accurately adjusted than when the sample passage is formed with a double-sided tape or a laminate film without an insulator. In addition, enzyme reaction reagents can be dispensed prior to the attachment of the middle plate to the lower plate. In a conventional biosensor, the reagents may undergo undesired chemical reactions with the double-sided tape or laminate film as they are dried. Thus, the application of the enzyme reaction reagents prior to the attachment prevents inaccurate measurement. That is, the uniform application of the reagents over the working electrode induces accurate reactions, increasing accuracy in analysis.

In the sample introduction channel 100, a sample is introduced into the biosensor as follows. When a sample is brought into contact with the sample entrance 101, a capillary phenomenon causes the sample to proceed through the sample entrance 101 into the sample passage. At this time, the sample collection barrier 501 serves to back the sample at the sample entrance. When collected in a sufficient amount, the sample flows through the sample entrance to the sample passage. After filling the sample passage 102, the sample is directed toward the air vent 103. Also, to prevent the formation of Air Packets at the intersection of the sample passage and the air vent, the void space 104 is further provided.

In the sample introduction channel of the biosensor according to the present invention, the sample introduction channel is not limited to the sample passage and air vent formed in the middle plate 200, but may be formed into different patterns.

Also, the insulator can be used to control the amount of the sample that is introduced into he sample passage. In detail, the amount of the blood sample can be controlled by adjusting the length of the corresponding sample passage formed in the lower insulator 500 to a desired extent. Whereas air is discharged outside because it is not affected by the insulator 500, a blood sample, which is hydrophilic, cannot move further forward when it meets the insulator 500. In this case, however, a blood sample flows along the upper plate, lacking an insulator, causing undesired results, such as the formation of air packets. Thus, as shown in FIGS. 3 and 4, an upper insulator 600 is preferably provided above the sample passage of the middle plate.

Figure 4:
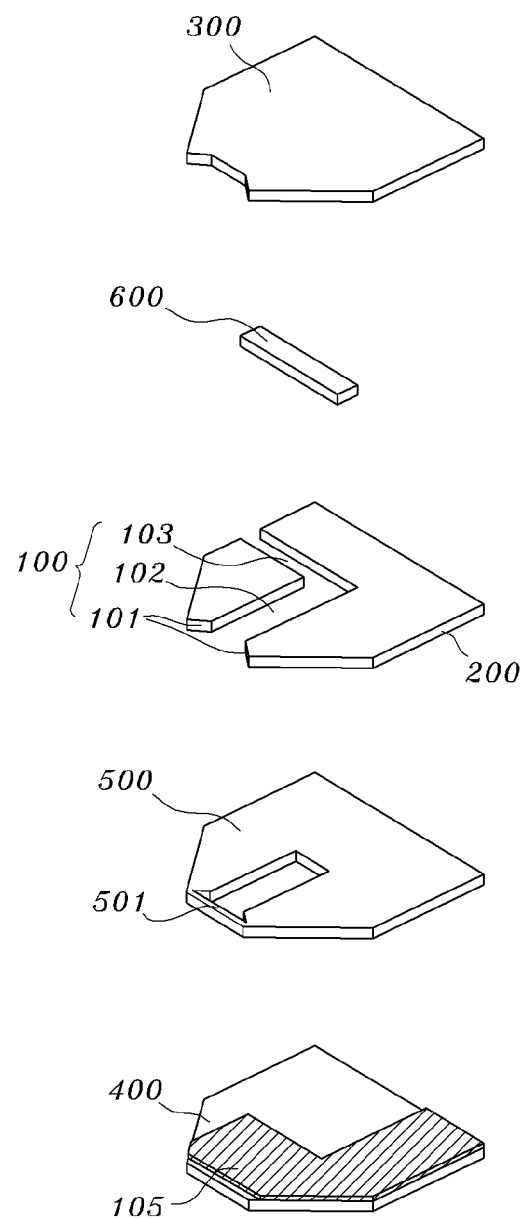
FIG. 4 is an exploded perspective view showing a sample introduction channel of an electrochemical biosensor in accordance with a further embodiment of the present invention.

FIGS. 3 and 4 show sample introduction channels of biosensors according to other embodiments of the present invention in exploded perspective views. In detail, the sample introduction channel of FIG. 3 comprises: a lower plate 400 upon which is constructed a working electrode coated with a reagent layer containing an electron transfer mediator and a redox enzyme; an insulator 500 provided with a sample collection barrier 501, screen-printed on the lower plate, having a sample passage pattern therein; a middle plate 200 provided with a sample introduction channel 100 consisting of a precut pattern of sample passage 102 and air vent 103, wherein the sample passage is crossed with the air vent, leaving a void space 104 at the cross, and sample entrance 101 having diagonal form became narrow toward the sample passage; an insulator 600 for preventing the migration of a sample to the air vent of the middle plate from the sample passage formed in both the middle plate and the insulator; and an upper plate (or cover) 300 for covering the sample introduction channel except for the sample introduction channel, all of said plates being layered in sequential order. In the case where respective insulators are provided above the upper layer and the lower plate, a desired amount of a sample can be confined even if the sample does not fill the air vent, which makes it possible to construct a sample instruction channel structure without a void space in the middle plate as in FIG. 4.

The structure of the sample introduction channel may be applicable to various types of biosensors, including, for example, a flat type biosensor in which a working electrode, an auxiliary electrode and a reference electrode are formed on the same plate, a converse-type biosensor in which a working electrode 105 formed on an upper plate faces a working electrode, or a differential type biosensor in which the flat type and the converse type are operated in a differential manner.

Figure 5:
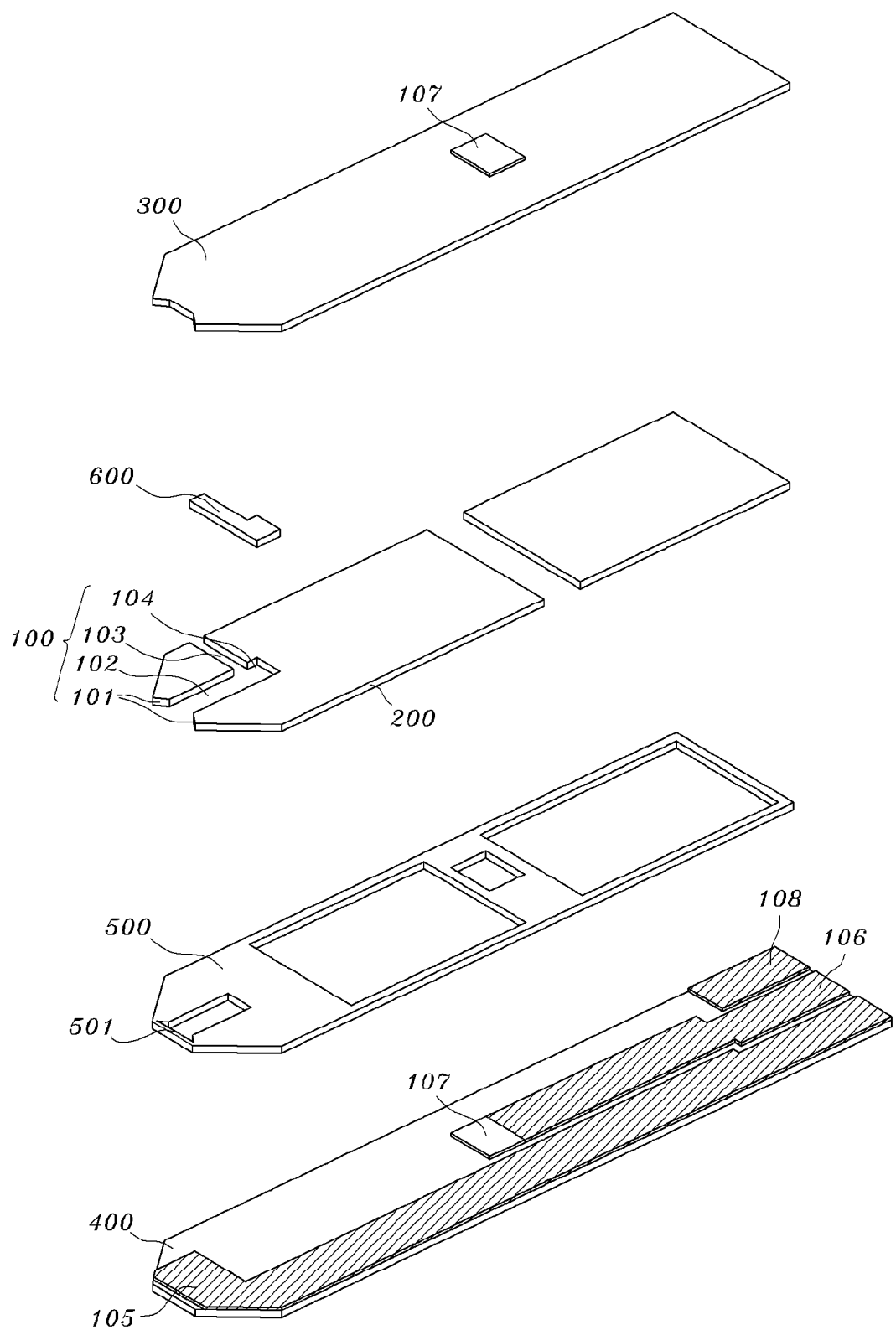
FIG. 5 is an exploded perspective view showing an electrochemical biosensor provided with a sample introduction channel in accordance with an embodiment of the present invention.

With reference to FIG. 5, a flat type biosensor provided with the above-mentioned structure of a sample introduction port in accordance with a preferable embodiment of the present invention is shown in an exploded perspective view. The flat type biosensor comprises a lower plate 400 on which is disposed an electrode unit including an electron transfer mediator/oxidation enzyme-fixed working electrode 105 and a reference electrode 106; a hydrophobic insulation lower plate 500, provided with a sample collection barrier 501, screen-printed on the lower plate, having a sample passage pattern therein; a middle plate 200 provided with a sample introduction channel 100 consisting of a cut-out pattern of a tapered sample entrance 101, a sample passage 102 and an air vent 103, wherein the sample passage is crossed with the air vent, leaving a void space 104 at the cross; an insulator 600 for preventing the migration of a sample to the air vent of the middle plate from the sample passage formed in both the middle plate and the insulator; and an upper plate (or cover) 300 for covering the sample introduction channel except for the sample introduction port?, all of said plates being layered in sequential order. In the sample introduction channel 100, preferably, the sample passage is crossed with the air vent and the sample entrance is gradually narrowed in the direction toward the sample passage. However, the sample introduction channel may vary in structure as mentioned above. Also, various conformations may be applicable to the upper insulator as well as the pattern of the lower insulator.

The electrochemical biosensor can be prepared as follows. First, converse-type electrodes (working electrode 104 and reference electrode 105) are printed or deposited with carbon or metal in the lengthwise direction of the strip on the lower plate 400. On this lower plate 400, the insulator 500 is deposited by screen printing in a pattern such that a part of the working electrode that is reacted with a sample is exposed. Then, an electron transfer mediator and an oxygenation enzyme are dispersed over and fixed onto the exposed part of the working electrode. Afterwards, the middle plate 200, provided with the pattern of the sample introduction channel 100, is attached at a height of hundreds of micrometers onto the insulator 500 layered on the lower plate 400, with the exposition of electrical connections only. Using an adhesive or double-sided tape, the lower plate 400 and the middle plate 200 may be attached to each other. Thereafter, the upper plate (or cover) 300 with the insulator 600 printed therebelow is pressed against the middle plate 200 using adhesive or double-sided tape.

The lower plate and the upper plate of the biosensor may be made of ceramic, a glass sheet, or a polymer, with preference for an organic polymer such as polyester, polyvinylchloride and polycarbonate.

Examples of the material for the insulators include urethanes and polyacrylates.

As for the electrodes including the reference electrode, the working electrode and the reference electrode, their materials are not specifically limited as long as they are electrically conductive. Examples of the electrical material suitable for the electrodes include silver epoxy, palladium, copper, gold, platinum, iridium, silver/silver chloride, carbon, and carbon modified with a specific redox pair or other additives. The reference electrode, the auxiliary electrode, and the working electrode can be formed through the screen printing, physical vapor deposition, and etching of conductive materials or through the attachment of conductive tape.

In the electrochemical biosensor, a blood sample is absorbed into the sample introduction channel through a capillary phenomenon. Thanks to the tapered sample entrance and the sample collection barrier present between the sample entrance and the sample passage, a sufficient amount of a blood sample can be uniformly introduced into the biosensor. In addition, the lower insulator can be screen printed in a predetermined pattern on the lower plate provided with an electrode unit, which is convenient for mass production. Also, the exposed area of the working electrode, which is reacted with a sample, can be adjusted accurately by screen printing, thus increasing the accuracy, reproducibility and reliability of measurement. The presence of insulators on both lower and upper sides of the sample passage allows the sample passage to be filled with a sample to a desired position, thereby increasing reproducibility and reliability of sample introduction.

As an electron transfer mediator, ferrocene or its derivatives, quinone or its derivatives, organic conducting salts, or viologen may be used. Preferably, the electron transfer mediator is a mixed-valence compound able to form a redox couple, including hexaammineruthenium (III) chloride, potassium ferricyanide, potassium ferrocyanide, DMF (dimethylferrocene), ferricinium, FCOOH (ferrocene monocarboxylic add), TCNQ (7,7,8,8-tetracyanoquinodimethane), TTF (tetrathiafulvalene), Nc (nickelocene), NMA+(N-methylacridinium), TTT (tetrathiatetracene), NMP+(N-methylphenazinium), hydroquinone, MBTHDMAB (3-dimethylaminobenzoic add), 3-methyl-2-benzothiozolinone hydrazone, 2-methoxy-4-allylphenol, AAP (4-aminoantipyrin), dimethylaniline, 4-aminoantipyrene, 4-methoxynaphthol, TMB (3,3',5,5'-tetramethylbenzidine), 2,2-azino-di-[3-ethylbenzthiazoline sulfonate], o-dianisidine, o-toluidine, 2,4-dichloro phenol, 4-aminophenazone, benzidine, and Prussian blue. Of these, hexaammineruthenium (III) chloride is preferred because its redox states in aqueous solutions are stable and reversible with insensitivity to pH and its formal potential is low enough (approximately −0.2~0.2V) to minimize the influence of various interfering components, such as ascorbic add, acetaminophen and uric rid.

Herein, it should be noted that the present invention, although described as being applied to biosensors for the analysis of blood glucose levels, can introduce appropriate enzymes and electron transfer mediators to the electrode system so that a variety of samples, including bio-materials, such as metabolites, e.g., cholesterol, lactate, creatinine, proteins, hydrogen peroxide, alcohols, amino acids, and enzymes, e.g., GPT (glutamate pyruvate transaminase) and GOT (glutamate oxaloacetate transaminase), environmental materials, agricultural and industrial materials, and food materials, can be quantitatively analyzed. That is, versatile metabolites can be analyzed for their levels once suitable enzymes are selected in concert with the electron transfer mediator. For instance, like glucose oxidase, used for the quantitative analysis of glucose level, lactate oxidase can be applied to lactate, cholesterol oxidase to cholesterol, glutamate oxidase to glutamate, horseradish peroxidase to hydrogen peroxide, and alcohol oxidase to alcohol.

A better understanding of the present invention may be grasped with reference to the following examples, which are set forth to illustrate, but are not to be construed to limit the present invention.

MODE FOR THE INVENTION

EXAMPLE

Fabrication of Biosensor

The same working electrode and electrical connection shown in FIG. 5 was constructed by screen printing carbon paste, followed by thermal treatment at 140° C. for 5 min. Then, silver paste was screen printed on the end of the electrical connection to the same thickness as that of the middle plate so as to complete a circuit connection. As for the electrode of the upper plate, carbon paste was screen printed and thermally treated under the same condition as in the electrode of the lower plate, to afford a reference electrode which also served as an auxiliary electrode. At the end of this reference electrode, a circuit connection was formed with silver paste so as to complete the construction of the upper plate electrode.

A piece of polyester-based double-sided tape was press-molded to have the same sample introduction channel shown in the middle plate of FIG. 5, which was composed of a sample entrance, a sample passage, an air vent and a void space. At this time, the sample passage and the air vent were adjusted to have a width ratio of 4:1. The total volume of the sample introduction channel was 0.2 μl.

Using a screen printing method, lower insulator 500, provided with the same sample collection barrier 501 shown in FIG. 5, was deposited over the lower plate on which the electrodes were constructed. Next, a mixed solution containing 0.015 mg of hexaammineruthenium (III), 0.015 mg of a dispersant (carboxymethylcellulose: CMC), 0.01 mg of a surfactant (brand name: Triton X-100) and 40 mg of glucose oxidase per 1 ml was dropped on the exposed electrodes on the sample passage, followed by thermal treatment at 45° C. for 30 min. after the enzyme mixture was completely dried, the middle plate was pressed to assemble it to the lower plate and covered with the upper plate in such a way that the electrode of the upper plate was aligned with a circuit connection.

Comparative Example

A converse-type biosensor was fabricated in the same manner as in the Example with the exception that the hydrophobic lower plate provided with the sample collection barrier was not deposited.

Experimental Example

Effect of the Sample Collection Barrier at Sample Entrance on Analysis Accuracy of Biosensor The sample collection barrier provided at the sample entrance of the biosensor was assayed for its effect on the analysis accuracy of the biosensor as follows.

Three blood samples were measured for glucose level (mg/dl) using a measuring apparatus typically used in hospitals (YSI 2300 stat plus), and the glucose levels thus measured were set as reference values. Separately, the blood samples were applied to the conserve-type biosensors fabricated in Example and Comparative Example to quantify glucose levels. This quantification was repeated five times, and the mean values, coefficient of variation, and standard deviation were calculated and are summarized in Table 1, below.

TABLE 1

| Glucose Levels(mg/ | Example | | | Comparatiave Example | | |
|---|---|---|---|---|---|---|
| dl) | Sample1 | Sample2 | Sample3 | Sample1 | Sample2 | Sample3 |
| Reference Values | 97 | 209 | 498 | 97 | 209 | 498 |
| Strip 1 | 97 | 208 | 493 | 89 | 218 | 479 |
| Strip 2 | 96 | 203 | 490 | 92 | 216 | 484 |
| Strip 3 | 96 | 207 | 494 | 94 | 208 | 502 |
| Strip 4 | 97 | 210 | 498 | 92 | 197 | 482 |
| Strip 5 | 98 | 206 | 488 | 95 | 203 | 455 |
| Mean | 97 | 207 | 493 | 92 | 208 | 479 |
| STDEV | 1.2 | 2.6 | 3.9 | 2.3 | 8.8 | 17.0 |
| CV | 1.2 | 1.3 | 0.8 | 2.5 | 4.2 | 3.5 |

When the blood samples were analyzed using the biosensor provided with the sample collection barrier in accordance with the present invention, as shown in Table 1, the mean values thereof were found be closer to the reference values with a CV (Coefficient of Variation) of 0.8-1.3 and an STDEV (Standard Deviation) of 1.2-3.9 than when using the biosensor lacking the sample collection barrier (Comparative Example) (CV: 2.5~4.2, STDEV: 2.3~17.0), indicating that the sample collection barrier can improve analysis accuracy.

INDUSTRIAL APPLICABILITY

Provided with the sample collection barrier at the sample entrance, therefore, the biosensor in accordance with the present invention can allow a sample to be introduced at higher accuracy and to be analyzed with higher reproducibility and reliability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An electrochemical biosensor, comprising: a lower plate, upon which is constructed a working electrode coated with a reagent layer containing an electron transfer mediator and a redox enzyme, and a reference electrode; a middle plate having a precut pattern defining a sample introduction channel composed of a sample entrance for introducing a sample into said electrochemical biosensor, a sample passage and an air vent ; a lower insulator located between the middle plate and the lower plate; an upper insulator located above the middle plate wherein the upper insulator roofs over the air vent, the upper insulator preventing migration of the sample into the air vent; and an upper plate or a cover that forms a sample cell structure,
   wherein the sample entrance is tapered and narrows toward the sample passage,
   wherein at least a portion of the working electrode is exposed in the sample passage for direct contact with a sample introduced into the sample entrance; the lower insulator has a precut pattern having the same structure as the precut pattern of the sample passage aligned therewith, the precut pattern of the lower insulator having a bottom wall extending across the sample passage on the same plane as the lower insulator and directly below the sample passage with a hydrophobic sample collection barrier located directly below the sample entrance and between the sample entrance of the middle plate and the lower plate such that the hydrophobic sample collection barrier does not further extend to be below the sample passage; and the hydrophobic sample collection barrier protrudes from the lower plate toward the sample entrance, the hydrophobic sample collection barrier having a predetermined height of 1 µm to 10 µm and extends across the sample entrance when the lower plate, lower insulator middle plate and upper plate are assembled.

2. The electrochemical biosensor according to claim 1, wherein the sample introduction channel has a precut pattern in which the sample passage is crossed with the air vent.

3. The electrochemical biosensor according to claim 1, wherein the precut pattern of the lower insulator is screen printed on the lower plate in a manner such that the precut pattern of the lower insulator have the same structure as the precut pattern of the sample passage and the air vent in the middle plate.

4. The electrochemical biosensor according to claim 1, wherein the lower insulator is made of a urethane or a polyacrylate.

5. The electrochemical biosensor according to claim 1, wherein the upper insulator is made of a urethane or a polyacrylate.

6. The electrochemical biosensor according to claim 1, wherein the precut pattern of the lower insulator has the same structure as the precut pattern of the sample passage, the air vent and a void in the middle plate.

7. The electrochemical biosensor according to claim 1, wherein the hydrophobic sample collection barrier has a lip positioned directly below the sample entrance once the sample is brought into contact with the sample entrance such that the lip backs the sample at the sample entrance.

8. The electrochemical biosensor according to claim 1, wherein said height of the hydrophobic sample collection barrier is the same as a thickness of the lower insulator.

9. An electrochemical biosensor, comprising: a lower plate, upon which is constructed a working electrode coated with a reagent layer containing an electron transfer mediator and a redox enzyme, and a reference electrode; a middle plate having a precut pattern defining a sample introduction channel composed of a sample entrance, a sample passage and an air vent; a lower insulator located between the middle plate and the lower plate; an upper insulator located above the middle plate wherein the upper insulator roofs over the air vent, the upper insulator preventing migration of the sample into the air vent; and an upper plate or a cover that forms a sample cell structure, wherein the sample entrance is tapered and narrows toward the sample passage, wherein at least a portion of the working electrode is exposed in the sample passage for direct contact with a sample introduced into the sample entrance; the lower insulator has a precut pattern with a hydrophobic sample collection barrier of a predetermined height of 1 to 10 µm located directly below the sample entrance of the middle plate and extending across the sample entrance such that the hydrophobic sample collection barrier does not further extend to be below the sample passage, the hydrophobic sample collection barrier having a lip positioned directly below the sample entrance once the sample is applied to the sample passage such that the lip backs the sample at the sample entrance to uniformly distribute the sample in the sample passage; wherein the lower insulator having the precut pattern is applied onto the lower plate, the precut pattern of the lower insulator having the same structure as the precut pattern of the sample passage in the middle plate and is aligned therewith.

* * * * *